United States Patent [19]

Cardarelli et al.

[11] Patent Number: 4,541,956
[45] Date of Patent: Sep. 17, 1985

[54] TIN STEROIDS AND THEIR USE AS ANTINEOPLASTIC AGENTS

[75] Inventors: Nathan F. Cardarelli; Sebastian V. Kanakkanatt, both of Akron, Ohio

[73] Assignee: Unique Technologies, Inc., Akron, Ohio

[21] Appl. No.: 518,073

[22] Filed: Jul. 28, 1983

[51] Int. Cl.$^4$ ................................................ C07J 9/00
[52] U.S. Cl. .............................. 260/397.1; 260/397.2; 260/397.4
[58] Field of Search ............................... 424/238, 243; 260/397.1, 397.2, 397.3, 397.4, 397.45, 397.47

[56] References Cited

U.S. PATENT DOCUMENTS 4,265,823 5/1981 Nobile .................................. 424/243

Primary Examiner—Elbert L. Roberts
Attorney, Agent, or Firm—Oldham, Oldham & Weber Co.

[57] ABSTRACT

A method and composition for the preparation of steroid compounds by the reaction of various organotin compounds with steroids. Said compounds retard the growth of malignant tumors and, in some cases, completely destroy the tumor.

3 Claims, No Drawings

TIN STEROIDS AND THEIR USE AS ANTINEOPLASTIC AGENTS

TECHNICAL FIELD

The present invention relates to a composition of, and preparation of, tin steroids, and their use as antineoplastic agents.

BACKGROUND ART

Heretofore, with regard to the treatment of malignant growths such as various types of cancer, and the like, the general approach of the medical and pharmaceutical professions has been keyed to the discovery of the causitive agents. The general approach by the pharmaceutical and medical industry has been to determine the nature of such agents, study the mechanism involved, and then create a pharmaceutical material that will intervene that mechanism.

It has now been discovered by the inventors that the thymus gland of mammals contains tin. Moreover, it has further been discovered that the thymic tin compounds are in steroid form, and that tin steroids retard the growth of and and even kill malignant tumors or prevent cancerous proliferation.

DISCLOSURE OF INVENTION

It is therefore an aspect of the present invention to produce tin steroids.

It is another aspect of the present invention to produce tin steroids, as above, through the reaction of an organotin compound and a steroid.

It is a further aspect of the present invention to produce tin steroids, as above, by a process which is generally straight-forward and in which generally no toxic or hazardous by-products or compounds are produced.

It is yet another aspect of the present invention to produce tin steroids, as above, for use as an antineoplastic agent.

It is yet another aspect of the present invention to produce tin steroids, as above, which can be orally administered.

It is yet another aspect of the present invention to produce tin steroids, as above, which have therapeutic value.

It is yet another aspect of the present invention to produce tin steroids, as above, which have prophylactic value.

These and other aspects of the present invention will become more apparent from the following detailed disclosure of the invention.

In general, a tin steroid compound, comprises the reaction product of an organotin compound and a steroid.

In general, an antineoplastic process comprises the steps of administering an organotin steroid to an animal, said tin steroid being therapeutic towards malignant tumors.

BEST MODE FOR CARRYING OUT THE INVENTION

The tin steroids of the present invention are produced by the reaction of an organotin compound with a steroid. Steroids have as a common nucleus, a fused-reduced 17 carbon atom ring system, cyclopentanoperhydrophenanthrene. The links of the side chains will vary and generally contain from 8 to 10 carbon atoms in the sterols, 5 carbon atoms in the bile acids, 2 carbon atoms in the adrenal cortical steroids, and none in the estrogens and androgens. Typically, the steroid utilized in the present invention has the following formula

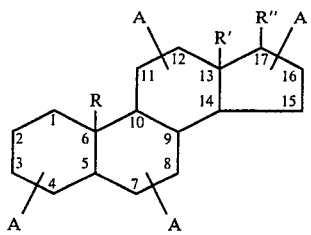

wherein R is hydrogen, or from 1 to 4 carbon atoms with either hydrogen or methyl being preferred. Similarly, R' is hydrogen or from 1 to 4 carbon atoms with hydrogen or methyl being preferred. R" can be hydrogen, oxygen, or from 1 to 12 carbon atoms, desirably, hydrogen, oxygen, or from 1 to 10 carbon atoms, with from 3 to 6 carbon atoms being preferred. The A group is either hydrogen or an alcohol, that is an OH group, and is usually located at the 3, 6, 12 or 17 position. Preferred steroids include cholic acid, deoxycholic acid, testosterone, cholesteryl chloride, dehydroisoandrosterone, estrone, dexamethasone, adrenosterone, betamethason, cholanic acid, cholesterol, and corticosterone.

The organotin compounds are represented by the formula:

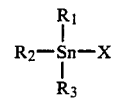

wherein $R_1$, $R_2$, and $R_3$ can be the same or different. $R_1$, $R_2$, and $R_3$ can be hydrogen or an alkyl group having from 1 to 6 carbon atoms, desirably from 3 to 5 carbon atoms, with 4 carbon atoms being preferred, an aromatic or an alkyl substituted aromatic having from 6 to 12 carbon atoms, such as a phenyl group, an aromatic substituted alkyl, for example a phenyl substituted alkyl wherein the alkyl group has from 7 to 12 carbon atoms, desirably from 9 to 11 and preferably 10 carbon atoms. X can be a hydroxy group, a halide, with chlorine being preferred, or a dicarboxylic acid group having from 2 to 10 carbon atoms with from 3 to 6 carbon atoms being preferred, such as adipic acid, succinic acid, or glutaric acid, an hydroxide oxide wherein $R_2$ and $R_3$ do not exist, or a monocarboxylic acid having from 2 to 6 carbon atoms, preferably 2 or 3 carbon atoms such as acetic acid. When X is a dicarboxylic acid, the acid will generally have the Sn, $R_1$, $R_2$, $R_3$ group extending off of both acid groups. Examples of preferred tin compounds include triphenyltin hydroxide, n-butyltin hydroxide oxide, triphenyltin chloride, tri-n-butyltin adipate, tri-n-butyltin chloride, hexamethylditin, n-propyltin trihalide, tri-n-butyltin fluoride, triethyltin halide, diethyltin halide, n-butyltin hydroxide oxide, trimethyltin halide, and triethyltin halide, with the first five-named compounds being preferred.

The tin steroids of the present invention are prepared by adding and dissolving the tin compound as well as the steroid in a mutually compatible solvent and heating. The solvent naturally is common to both compounds and also is inert thereto. Generally, a variety of solvents can be utilized such as alcohols having from 1 to 6 carbon atoms, preferably from 1 to 3 carbon atoms. Preferred compounds include chloroform, methanol, ethanol, and the like. The temperature to which the solution is heated is generally limited by the boiling point of the solvent. Generally, the reaction is carried out at a temperature of from about 60° to about 100° C., with from about 75° to about 85° C. being preferred. One particular manner of carrying out the reaction is to reflux the solution for a period of time, for example, a couple or ten hours. The reaction product can then be filtered and evaporated to remove most of the solvent and then cooled to beneath the melting point of the product to obtain the product. The molecular weight range of the organotin steroid compound generally is from about 400 to about 1,200, with from about 400 to about 800 being preferred.

The present invention is a clean system in that no foreign ingredients are utilized and thus a relatively pure product is produced. Moreover, the product has no toxicants, harmful by-products or other undesirable components therein in that the reaction generally yields either water or hydrochloric acid which can readily be removed.

The tin steroid compounds of the present invention can be utilized as antineoplastic inasmuch as they have tumor suppressing properties. Moreover, some of the compounds have even been found to kill malignant tumors. As such, the tin steroid compounds of the present invention have therapeutic value as well as prophylactic value. They also are non-toxic and a non-irritant with regard to the test animal.

Various tin steroids, according to the present invention were tested against mouse adenocarcinoma. To better illustrate the nature and application of these compounds, a number of examples are given.

EXAMPLE 1

Triphenyltin hydroxide, in an amount of 3.67 g, was dissolved in 100 ml of ethanol, and 4.265 g of cholic acid were dissolved in 100 ml of ethanol. Both solutions were mixed in a 250 ml round bottomed flask with a soxhlet and a reflux condenser, and heated to boiling. The mixture was refluxed for two hours at 78° to 80° C. The reaction product was filtered and evaporated to one-fourth of its volume ~50 ml, then refrigerated at 6° C. to get crystals of the products.

| Appearance: | White flaky solid |
|---|---|
| Melting Point: | 123–127° C. |
| Molecular Weight (determined by mass spectrometer) = 720 | |
| Structure: | |

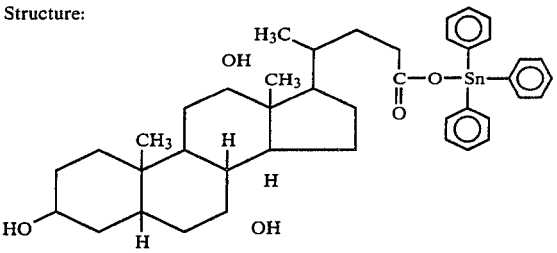

Triphenyltin cholate was evaluated against transplanted tumor fragments (mammary adenocarcinoma) in AKI strain cancer-prone mice at 10 ppm and 100 ppm administered continuously and ad libitum in drinking water. Results are shown in Table I. Twenty mice were used, 10 male and 10 female, in each cohort; with three cohorts-0 ppm(control), 10 ppm and 100 ppm dosage regimen. Thirty days post transplant mice were sacrificed, the tumor and the tissues were extirpated and weighed. External tumor size measurements were made during the course of the experiment.

TABLE I

TRIPHENYLTIN CHOLATE EFFECT ON TUMOR GROWTH

| Cohort | No. Mice | Agent Regimen | Average Tumor Wt. | No. Tumors | % Tumor as a Part of body wt. | Growth Suppression Factor |
|---|---|---|---|---|---|---|
| 1 | 20 | 100 ppm | 0.1917 g | 20 | 1.35% | 6.26 |
| 2 | 20 | 10 ppm | 1.4281 g | 31 | 6.26% | 0.84 |
| 3 | 20 | 0 ppm | 1.2005 g | 32 | 4.95% | 1.00 |

The suppression effect is seen to be dose dependent.

At necropsy, organs were examined for signs of intoxication. Liver, spleen, thymus and gastrointestinal tract were normal. No gross effects of intoxication were present. Weight gain was normal over the course of the experiment.

*Measured as $\dfrac{\text{Tumor weight of controls mice}}{\text{Tumor weight of test mice}}$

EXAMPLE 2

CHOLESTERYL-n-BUTYL STANNATE 2.07 g of n-butyltin hydroxide oxide were dissolved in 90 ml of chloroform (partially dissolved in the cold); 3.86 g of cholesterol was dissolved in 90 m of chloroform. The solutions were mixed in a 200 ml round bottomed flask fitted with a soxhlet and a reflux condenser and heated to boiling. The mixture was refluxed for three hours at 61° to 63° C. The reaction product in solution was filtered and evaporated to about 40 ml, then cooled at 6° C.

| Appearance: | White powder |
|---|---|
| Melting Point: | 135–141° C. |
| Calculated M.W.: | 557 |
| M.W. by spectroscopy: | 520 |
| Structure: | |

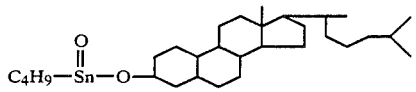

Mice provided with this material at 10 ppm and 100 ppm over a six week period showed no signs of intoxication before sacrifice or a necropsy.

EXAMPLE 3

TRIPHENYLTIN TESTOSTERONYL ETHER 3.5 g of triphenyltin chloride was dissolved in 40 ml of ethanol and 2.8 g of testosterone was dissolved in 40 ml of ethanol. Both solutions were mixed in a 200 ml round bottom flask fitted with a soxhlet and a reflux condenser. The mixture was refluxed for 3 hours at 78°–80° C. The reaction product was filtered and evaporated to ¼ its volume, then cooled to form a powder.

Appearance: amorphous powder
Melting point: 75–80° C.
MW (determined by mass spec) - 720

Structure:

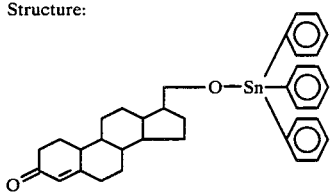

This compound was administered to mice in a manner similar to that described in Example 1. No toxic symptoms were evident prior to sacrifice nor upon examination of major organ systems at necropsy. Effects on tumor development are shown in Table II.

TABLE II
TRIPHENYLTIN TESTOSTERONYLETHER EFFECT ON TUMOR GROWTH

| Cohort | No. Mice | Agent Regimen | Average Tumor Wt. | No. Tumors | % Tumor as a Part of body wt. | Growth Suppression Factor |
|---|---|---|---|---|---|---|
| 1 | 20 | 100 ppm | 0.573 t | 19 | 2.00% | 2.1 |
| 2 | 20 | 10 ppm | 0.541 g | 25 | 1.89% | 2.2 |
| 3 | 20 | 0 ppm | 1.2005 g | 32 | 4.95% | 1.00 |

In one case of 20, the tumor transplant was destroyed by the agent.
During the 30 day observation period, and upon necropsy, no toxicological alterations were evident.

EXAMPLE 4
TRIBUTYLTIN DEOXYCHOLATE 7.04 g of tributyltin adipate was partially dissolved in 40 ml of ethanol and 3.98 g of deoxycholic acid was dissolved in 40 ml of ethanol. Both solutions were mixed in a 200 ml round bottomed flask fitted with a soxhlet and a reflux condenser, and heated to boiling. The mixture was refluxed for three hours at 78° to 80° C. The reaction product was filtered and evaporated to one-fourth of its volume ~ 20 ml, then cooled to form the product.

| Appearance: | White crystalline solid |
|---|---|
| Melting Point: | 100–104° C. |
| Molecular Weight: | 682.5 |
| Structure: | |

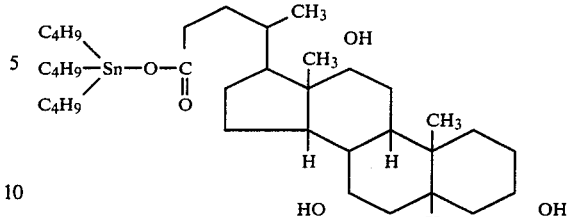

This primitive monoclinic crystal has the following cell parameters:

| a = 9.996A° | 2 = 90.454° |
|---|---|
| b = 10.344A° | B = 94.214° |
| c = 17.886A° | r = 90.780° |
| Volume 1844.084 A°3 | |

This material was examined against transplanted tumors in AKI mice with the effect noted in Table III.

TABLE III
TRIBUTYLTIN DEOXYCHOLATE EFFECT ON TUMOR GROWTH

| Cohort | No. Mice | Agent Regimen | Average Tumor Wt. | No. Tumors | % Tumor as a Part of body wt. | Growth Suppression Factor |
|---|---|---|---|---|---|---|
| 1 | 20 | 100 ppm | 0.64 g | 23 | 3.85% | 1.88 |
| 2 | 20 | 10 ppm | 0.75 g | 24 | 2.86% | 1.60 |
| 3 | 20 | 0 ppm | 1.2005 g | 32 | 4.95% | 1.00 |

In cohort 1, five mice of the 20 subjects were completely free of tumors, i.e., agent destroyed 25 percent of the implanted tumors.
No toxic symptoms were observed during the observation period or after necropsy. Weight gain was normal in all cases, and liver, spleen, thymus and G.I. tract showed no pathological alterations.

As apparent from Examples 1 through 4, the organotin compounds of the present invention are at least effective as a tumor growth suppressant and, in one case, even completely killed the cancerous growth.

Examples 5 through 14 relate to preparation of other tin steroid compounds of the present invention.

EXAMPLE 5
TRIPHENYLTIN CHOLESTERYL ETHER 3.67 g of triphenyltin hyroxide was dissolved in 80 ml of ethanol and 3.86 g of cholesterol was dissolved in 80 ml of ethanol. Both solutions were mixed in a 200 ml round bottom flask fitted with a soxhlet and reflux condenser, and heated to boiling. The mixture was refluxed for three hours at 78° to 80° C. The reaction product was filtered giving two fractions—a solid residue, dried at room temperature and a second material isolated by evaporation of the filtrate. Physical properties of the ethanol soluble species are:

| | Ethanol Soluble |
|---|---|
| Appearance: | white solid |
| Molec. weight | 736 |

-continued

| | Ethanol Soluble |
|---|---|
| Melting point | 119–121° C. |
| Structure: | |

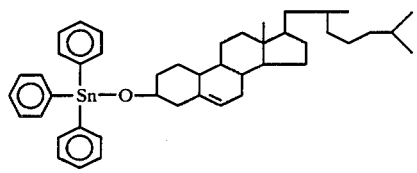

EXAMPLE 6
CHOLYL-n-BUTYL STANNATE 2.07 g of n-butyltin hydroxide oxide and 4.265 g of cholic acid were dissolved in 80 ml of ethanol. The mixture was refluxed for 20 hours at 78°–80° C. in a round bottomed flask fitted with a soxhlet and a reflux condenser. The reaction product was filtered and evaporated to one-fourth its volume, then cooled in a refrigerator to form crystals.

| Appearance: | White crystalline solid |
|---|---|
| Melting Point: | 205–218° C. |
| Calculated M.W.: | 571.5 |
| Structure: | |

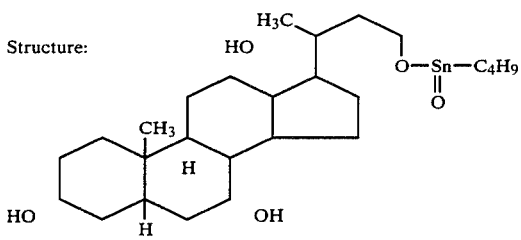

EXAMPLE 7
CHOLESTERYL TRIBUTYLTIN ETHER 7.04 g of tributyltin adipate and 4.05 g of cholesteryl chloride were dissolved in 80 ml of ethanol in a 200 ml round bottomed flask fitted with a soxhlet and a reflux condenser. The solution was refluxed at 78°–80° C. for eight hours. The reaction product was filtered, giving two fractions—SVK 8 is the filtrate. The filtrate was evaporated to 10 ml and cooled in a refrigerator to form crystals.

| Appearance: | partially crystalline off-white powder |
|---|---|
| Melting Point: | 83–85° C. |
| Calculated M.W.: | 959 |
| Structure: | |

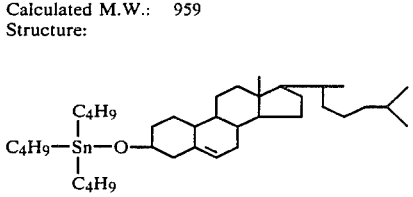

EXAMPLE 8
CHOLESTERYL TRIBUTYLTIN ADIPATE (FRACTION-2)

7.04 g of tributyltin adipate and 2.8666 g of cholesterol were dissolved in 80 ml of ethanol in a 200 ml round bottomed flask fitted with a soxhlet and a reflux condenser. The solution was refluxed for eight hours at 78°–80° C. The SVK-9 the filtrate. The filtrate was evaporated to one-fourth its volume and then cooled in a refrigerator. The residue was dried at room temperature. Two fractions were separated.

| | Fractions | |
|---|---|---|
| | 1. (ethanol soluble) | 2. (ethanol insoluble) |
| Appearance | white crystalline flakes | white crystalline powder |
| Melting Point | 96–98° C. | 91–93° C. |
| Molecular wt. | 666 | 915 |

Structure of Fraction 1:

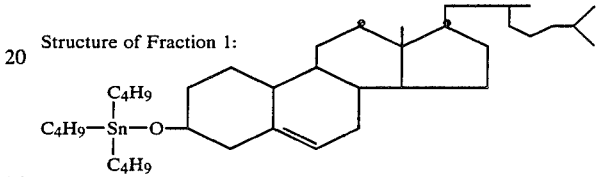

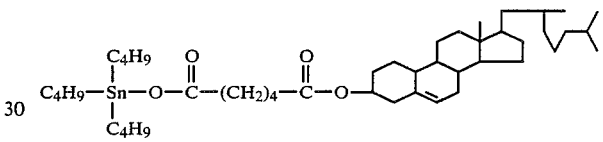

EXAMPLE 9
TRIBUTYLTIN CHOLATE 3.25 g of tri-n-butyltin chloride and 4.08 g of cholic acid were dissolved in 80 ml of ethanol in a 200 ml round bottom flask fitted with a soxhlet and a reflux condenser. The solution was refluxed for 8 hours at 78°–80° C. The reaction product was filtered (residue was discarded), evaporated to about 10 ml, and cooled by refrigeration at 6° C.

| Appearance: | white amorphous solid |
|---|---|
| Melting Point: | 89–91° C. |
| Calculated MW: | 715.0 |
| Structure: | |

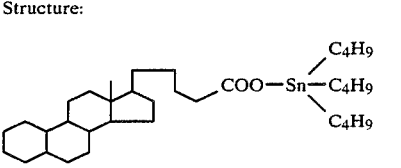

EXAMPLE 10
TESTOSTERONYL-n-BUTYL STANNATE 2.07 g of n-butyltin hydroxide oxide and 2.88 g of testosterone were dissolved in 80 ml of ethanol in a 200 ml round bottom flask fitted with a soxhlet and a reflux condenser. The solution was refluxed at 78°–80° C. for three hours. The reaction product was filtered and evaporated to dryness. The solid was recrystallized in ethanol.

| Appearance: | yellow crystals |
|---|---|
| Melting Point: | 90°–95° C. |

Calculated MW: 477.43
Structure:

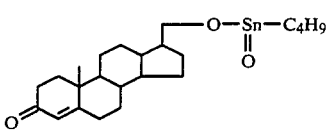

EXAMPLE 11
TRIPHENYLTIN TESTOSTERONYL ETHER 3.67 g of triphenyltin hydroxide, 2.88 g of testosterone and 2.50 g of methylenedi-p-phenyl diisocyanate were dissolved in 80 ml of ethanol in a 200 ml round bottom flask fitted with a soxhlet and a reflux condenser. The solution was refluxed at 78°-80° C. or three hours. The reaction product was filtered and evaporated to dryness. The solid was recrystallized in ethanol.

| Appearance: | yellow amorphous solid |
| Melting Point: | 95°-98° C. |
| Calculated MW: | 887.43 |

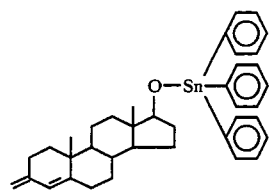

EXAMPLE 12
TRIPHENYLTIN DEHYDROISOANDROSTERONYL METHYLENE DI-P PHENYLDIAMIDE 2.47 g of dehydroisoandrosterone, 3.67 g of triphenyltin hydroxide, and 2.50 g methylenedi-p-phenyl diisocyanate were dissolved in 80 ml of ethanol in a 200 ml round bottom flask fitted with a soxhlet and a reflux condenser. The solution was refluxed at 78°-80° C. for three hours. The reaction product was filtered and evaporated to dryness. The solid was recrystallized in ethanol.

| Appearance: | yellow amorphous solid |
| Melting Point: | 90°-95° C. |
| Calculated MW: | 799.4 |

Structure:

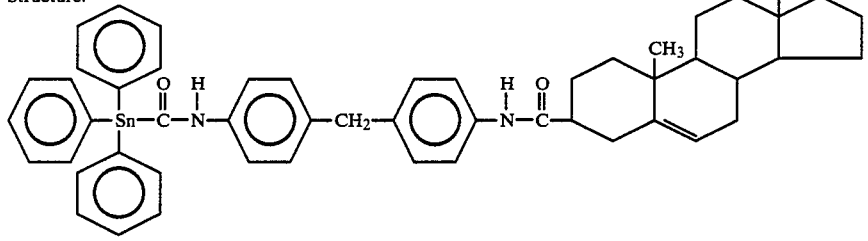

EXAMPLE 13
ESTRONYL-n-BUTYL STANNATE 2.07 g of n-butyltin hydroxide oxide and 2.70 g of estrone were combined in 80 ml of ethanol in 200 ml round bottom flask fitted with a soxhlet and a reflux condenser. The solution was refluxed for three hours at 78°-80° C. The reaction product was filtered and evaporated to dryness. The solid was recrystallized in ethanol.

| Appearance: | partially crystalline yellow solid |
| Melting Point: | 205°-208° C. |
| Calculated MW: | 459.36 |
| Structure: | |

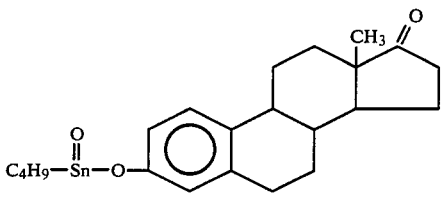

EXAMPLE 14
TRIMETHYLTIN CHOLATE 1.63 g of hexamethylditin and 4.085 g of cholic acid were dissolved in 80 ml of ethanol in a 200 ml round bottom flask fitted with a soxhlet and a reflux condenser. The solution was refluxed for two hours at 78°-80° C. The reaction product was filtered, evaporated to dryness, and recrystallized in ethanol.

| Appearance: | partially crystalline white solid |
| Melting Point: | 90° C.-92° C. |
| Calculated MW: | 571 |
| Structure: | |

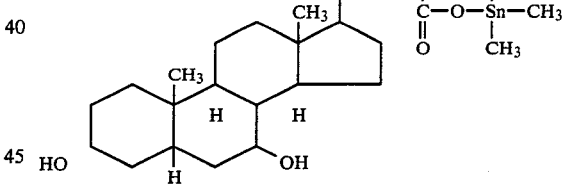

The dosage required for treatment of animals such as mice is from about 1.7 μg/g body weight to about 100 g/g body weight, with from about 25 μg/g body weight to about 50 μg/g body weight being preferred where μ is one microgram. Based upon a weight scale factor, the expected concentration with regard to human beings is expected to be 0.0125 g to 0.025 g per day based on 160 pound human weight. Such dosage can be administered on a periodic basis in the form of a pill or with a liquid, e.g., water.

While in accordance with the patent statutes, the best mode and preferred embodiment has been described in detail, the invention is not to be limited thereby, the scope of the invention being limited solely by the scope of the attached claims.

What is claimed is:

1. A tin steroid compound,
said tin steroid compound being the reaction product of a steroid compound and a tin compound, wherein said steroid compound is selected from the group consisting of cholic acid, testosterone, deoxycholic acid, cholesteryl chloride, cholesterol, and dehydroxycholesterol, and

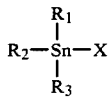

wherein $R_1$, $R_2$ and $R_3$ can be the same or different, wherein said $R_1$, $R_2$ and $R_3$ are selected from the group consisting of hydrogen, an alkyl having from 1 to 6 carbon atoms, a cycloalkyl having from 4 to 10 carbon atoms, an aromatic or an alkyl substituted aromatic having from 6 to 12 carbon atoms, and an aromatic substituted alkyl having from 7 to 12 carbon atoms, and wherein X is selected from the group consisting of hydroxyl, halide, hydroxide oxide wherein $R_2$ and $R_3$ do not exist, a dicarboxylic acid having from 2 to 10 carbon atoms, and a monocarboxylic acid having from 2 to 6 carbon atoms.

2. A tin steroid compound according to claim 1, wherein said tin compound is selected from the group consisting of triphenyltin hydroxide, n-butyltin hydroxide oxide, triphenyltin chloride, tri-n-butyltin adipate, tri-n-butyltin chloride, hexamethylditin, n-propyltin trihalide, tri-n-butyltin fluoride, triethyltinhalide, diethyltin halide, n-butyltin hydroxide oxide, trimethyltin halide, and triethyltin halide.

3. A tin steroid compound according to claim 1, wherein said tin compound is selected from the group consisting of triphenyltin hydroxide, n-butyltin hydroxide, triphenyltin chloride, tri-n-butyltin adipate, and tri-n-butyltin chloride.

* * * * *